May 23, 1972 W. H. JESSEL, JR., ET AL Plant Pat. 3,183
CHRYSANTHEMUM PLANT
Filed July 27, 1970
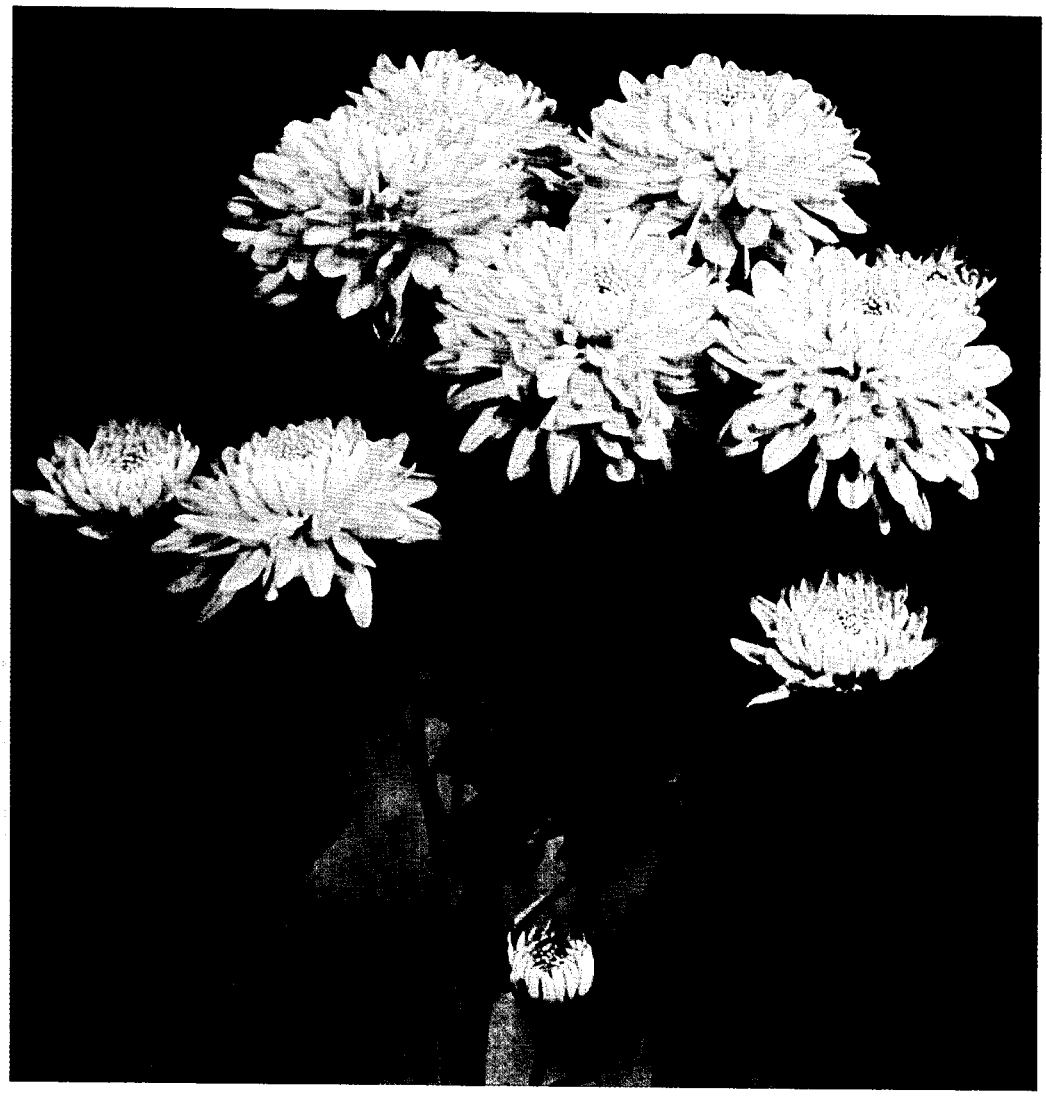
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,183
Patented May 23, 1972

3,183
CHRYSANTHEMUM PLANT

Walter H. Jessel, Jr., Doylestown, and William E. Duffett, Akron, Ohio, assignors to Yoder Brothers, Inc., Barberton, Ohio

Filed July 27, 1970, Ser. No. 58,749
Int. Cl. A01h *5/00*
U.S. Cl. Plt.—79 1 Claim

The present invention comprises a new and distinct variety of pompon chrysanthemum plant which is a sport of a light pink seedling identified for breeding purposes as YB 63340–1.

The new variety is similar in many respects to Belair, a commercial variety of Yoder Brothers, Inc., Barberton, Ohio, for which application for U.S. Letters Patent is concurrently being made. The Belair variety is a darker pink mutation of the above identified seedling, and both Belair and the present variety have the same characteristics of:

(1) Growth habit.
(2) Nine week response.
(3) Flower production.
(4) Lateral flowering down the stem.
(5) Flower form.

The new variety is distinguished from Belair by the following characteristics, with the comparison being based on growth under identical culture and conditions:

(1) A unique orange-bronze color previously unavailable in a pompon chrystanthemum.
(2) Light orange-bronze color.

The new variety is distinguished from Bronzechip, an unpatented but commercially well established variety of Yoder Brothers, Inc., by the following characteristics:

(1) A unique orange--bronze color previously unavailable in a pompon chrysanthemum.
(2) Increased flower production per stem, with 20–25% more of the stems producing 5–7 or more flowers per spray than Bronzechip.
(3) More flowers produced from laterals down the stem rather than on a similar plane at the top of the spray like Bronzechip.
(4) A more open spray formation than Bronzechip.
(5) Produces more shoots or breaks from a pinch, averaging 2–3 more shoots per plant than Bronzechip. This trait is even more prevalent during high temperature periods when Bronzechip is inclined to exhibit non-breaking tendencies.
(6) Average fresh weight per stem is 15–20% heavier than Bronzechip.
(7) Foliage less serrated than Bronzechip.
(8) A more uniform response in all periods, combined with an earlier response of approximately 5–7 days in summer and early fall (high temperature periods) than Bronzechip.

The new variety was discovered upon examination of a flowering block of the parent variety.

The new variety has been asexually reproduced by cuttings at Barberton, Ohio, and has been found to retain its distinctive characteristics through successive propagations.

My new variety when grown in the vicinity of Salinas, Calif.; Fort Myers, Fla. and Barberton, Ohio has a response period of approximately 9 weeks. It will be understood that the response time and blooming period may vary significantly with varying environmental conditions such as temperature, light intensity and day length. Suggested flowering in most of the United States is from April through November and for southern Florida, from December through April.

The following detailed response information and subsequent data is based on observations made of the new variety in a greenhouse in Barberton, Ohio. The response period is approximately 9 weeks, with response being accelerated to 8½ weeks under spring conditions and slowed to 9½ weeks in mid-summer and early fall under high temperature conditions. By way of comparison, Bronzechip will generally respond in approximately 9½ weeks, will accelerate its response to 8½ weeks under spring conditions, but will slow its response to 10 weeks under summer and fall high temperature conditions.

The accompanying drawing shows the color and form of my new variety, with the colors being as true as possible with color illustrations of this type.

The following is a detailed description of my new variety, with the color references being to the Munsell Color Chart, 1963 edition, and comparisons made with the variety Bronzechip.

Botanical classification: *Chrysanthemum morifolium.*

| | Bronze Belair | Bronzechip |
|---|---|---|
| Bloom: | | |
| Size | 2½″ | 2½″. |
| Fully expanded | 3″ | 3″. |
| Borne | Terminal cluster of 8–12 on elongated pedicels according to culture. | 3″. |
| Stems | Elongated pedicels 6″–10″ in length branching from main stem. | 3″. |
| Form | Decorative | 3″. |
| Permanence | 7–10 days | 3″. |
| Color: | | |
| Center of flower | Orange to light bronze, 2.5YR5/10 to 10YR8/10. | Light bronze, 2.5Y7/6. |
| Base of petals | Bronze, 2.5Y5/10 | Yellow bronze, 2.5Y8/6. |
| Inside of petals | Bronze to light bronze, 2.5Y5R/10 to 10YR8/10. | Yellow bronze, 2.5Y8/6 to light yellow 2.5Y8.5/4. |
| Reverse of petals. | 2.5Y8.5/6 to light yellow. | Pale yellow, 2.5Y9/4. |
| Tonality from a distance. | Orange bronze to light bronze. | Bronze to light bronze. |
| Discororation | Light bronze, 10YR8/10. | 2.5Y8.5/4, light yellow. |

*Petals.* — Texture — smooth; appearnce — slightly open at base, keeled at mid-point; form—tapers to a blunt point; arrangement—composite, whorled on a single receptacle; persistence—shatter resistant; fragrance—typical chrysanthemum.

*Reproductive organs.*—Stamens, anthers—none to 20 more or less depending on culture; pollen—none to scant; arrangement—center of flower if present; styles—present in both ray and disc florets; length—short; ovaries—at base of petals attached to receptacle.

*Plant.* — Form — herbaceous; growth — upright; height—36″ to 42″ depending on culture.

| | Bronze Belair | Bronzechip |
|---|---|---|
| Foliage: | | |
| Top side | Green, 7.5GY3/4 | Green, 7.5GY3/4. |
| Size | 7″–9″ long, 4″–5″ wide. | 6½″–8½″ long, 4″–5″ wide. |
| Quantity | Numerous | Numerous. |
| Shape | Palmate | Palmate. |
| Texture | Coarse | Coarse. |
| Ribs and veins | Prominent | Prominent. |
| Edge | Deeply indented | Deeply indented. |
| Serration | Slight | Very slight. |
| Underside | Light green, 5GY4/4 | Light green, 7.5GY4/4, darker than Bronze Belair. |
| Stipules | Prominent at base of petiole. | Rudimentary at base of petiole. |

I claim:

1. A new and distinct variety of pompon chrysanthemum characterized particularly as to novelty by a unique orange-bronze color, greater flower production per stem, an open terminal spray, lateral flowering down the stem, excellent breaking action on pinched crops during high temperature periods, and a uniform response at all periods, with an earlier response during high temperature periods.

No references cited.

ROBERT E. BAGWILL, Primary Examiner

UNITED STATES PATENT OFFICE

CERTIFICATE OF CORRECTION

Patent No. PP 3,183 Dated May 23, 1972

Inventor(s) Walter H. Jessel, Jr. and William E. Duffett

It is certified that error appears in the above-identified patent and that said Letters Patent are hereby corrected as shown below:

In column 1, delete lines 28-29 and substitute therefor: --1. One fourth (1/4")to one half inch (1/2") smaller flower than Belair.--

In column 2, line 32 opposite Borne; line 34 opposite Stems; line 36 opposite Form and line 37 opposite Permanence delete 3" under Bronzechip in each line.

In column 2, approximately line 42, adjacent the heading "Inside of petals" and under the heading "Bronze Belair", change "2.5Y5R/10" to --2.5YR5/10--.

In column 2, approximately line 47, change "Discororation" to --Discoloration--.

Signed and sealed this 23rd day of October 1973.

(SEAL)
Attest:

EDWARD M.FLETCHER,JR.
Attesting Officer

RENE D. TEGTMEYER
Acting Commissioner of Patents

Dedication

PP. 3,183.—*Walter H. Jessel, Jr.*, Doylestown, and *William E. Duffett*, Akron, Ohio, CHRYSANTHEMUM PLANT. Patent dated May 23, 1972. Dedication filed Feb. 6, 1975, by the assignee, *Yoder Brothers, Inc.* Hereby dedicates to the Public the entire remaining term of said patent.

[*Official Gazette July 1, 1975.*]